(12) United States Patent
Finne

(10) Patent No.: US 8,569,477 B2
(45) Date of Patent: Oct. 29, 2013

(54) METHOD FOR ISOLATING NUCLEIC ACIDS COMPRISING THE USE OF ETHYLENE GLYCOL MULTIMERS

(75) Inventor: Erling Sigurd Finne, Hvalstad (NO)

(73) Assignee: Life Technologies AS, Carlsbad, CA (US)

( * ) Notice: Subject to any disclaimer, the term of this patent is extended or adjusted under 35 U.S.C. 154(b) by 216 days.

(21) Appl. No.: 11/815,967

(22) PCT Filed: Feb. 13, 2006

(86) PCT No.: PCT/GB2006/000484

§ 371 (c)(1), (2), (4) Date: Oct. 10, 2008

(87) PCT Pub. No.: WO2006/085104

PCT Pub. Date: Aug. 17, 2006

(65) Prior Publication Data

US 2009/0069554 A1   Mar. 12, 2009

Related U.S. Application Data

(60) Provisional application No. 60/654,958, filed on Feb. 23, 2005.

(30) Foreign Application Priority Data

Feb. 11, 2005  (GB) .................................. 0502887.3
Feb. 17, 2005  (GB) .................................. 0503339.4

(51) Int. Cl.
  *C07H 21/02* (2006.01)
  *C07H 21/00* (2006.01)

(52) U.S. Cl.
  USPC ...................................... 536/25.4; 536/25.42

(58) Field of Classification Search
  None
  See application file for complete search history.

(56) References Cited

U.S. PATENT DOCUMENTS

| 4,336,173 A | 6/1982 | Ugelstad |
| 4,459,378 A | 7/1984 | Ugelstad |
| 4,654,267 A | 3/1987 | Ugelstad et al. |
| 5,234,809 A | 8/1993 | Boom et al. |
| 5,665,554 A * | 9/1997 | Reeve et al. ....................... 435/6 |
| 5,705,628 A | 1/1998 | Hawkins |
| 5,707,812 A | 1/1998 | Horn et al. |
| 5,898,071 A | 4/1999 | Hawkins |
| 5,990,301 A * | 11/1999 | Colpan et al. ................. 536/25.4 |
| 6,274,371 B1 * | 8/2001 | Colpan .......................... 435/259 |
| 6,297,371 B1 * | 10/2001 | Colpan et al. ................. 536/25.3 |
| 6,534,262 B1 | 3/2003 | McKernan et al. |
| 7,229,810 B2 * | 6/2007 | Sherman et al. .............. 435/188 |
| 7,553,658 B2 * | 6/2009 | Kepka et al. .................. 435/270 |
| 2001/0009148 A1 | 7/2001 | Asada et al. |
| 2004/0185449 A1 | 9/2004 | Quinn et al. |
| 2004/0197780 A1 | 10/2004 | McKernan et al. |

FOREIGN PATENT DOCUMENTS

| EP | 106873 | 11/1983 |
| EP | 1162364 | 12/2001 |
| EP | 1859038 | 8/2010 |
| JP | 09303232 | 11/1997 |
| JP | 00515385 | 11/2000 |
| WO | WO-91/12079 | 8/1991 |
| WO | WO-02055727 A2 | 7/2002 |

OTHER PUBLICATIONS 0670972.2, "Response to Jul. 6, 2009 Office Action", Filed on Nov. 16, 2009.
Abramson, Richard D. et al., "Nucleic acid amplification technologies.", *Current Opinion in Biotechnology*, vol. 4(1) 1993 , pp. 41-47.
Banerjee, S. K. et al., "Microwave-Based DNA Extraction from Paraffin-Embedded Tissue for PCR Amplification", *Biotechniques* 18 1995 , 768-772.
PCT/GB2006/000484, "International Search Report", Apr. 18, 2006, 3.

* cited by examiner

*Primary Examiner* — Lawrence E Crane

(57) ABSTRACT

The present invention provides a method of isolating nucleic acid from a sample, said method comprising contacting said sample with a solid support, preferably magnetic beads, in the presence of an ethylene glycol multimer consisting of from 2 to 70 ethylene oxide monomers, preferably tetraethylene glycol, whereby soluble nucleic acid in said sample is bound to the surface of the support, and separating said support with bound nucleic acid from the sample. Kits for performance of the invention are also provided.

36 Claims, 6 Drawing Sheets

METHOD FOR ISOLATING NUCLEIC ACIDS COMPRISING THE USE OF ETHYLENE GLYCOL MULTIMERS

CROSS-REFERENCE TO RELATED APPLICATIONS

This application is being submitted as a U.S. 35 U.S.C. 371 of International Application No. PCT/GB2006/000484, filed Feb. 13, 2006, which claims priority to GB Application No. 0602887.3, filed Feb. 11, 2005, GB Application No. 0503339.4, filed Feb. 17, 2005 and U.S. Application No. 60/654,958, filed Feb. 23, 2005, all of which are incorporated herein by reference in their entireties.

The present invention relates to the isolation of nucleic acid, and especially to the isolation of DNA or RNA from samples.

The isolation of DNA or RNA is an important step in many biochemical and diagnostic procedures. For example, the separation of nucleic acids from the complex mixtures in which they are often found is frequently necessary before other studies and procedures e.g. detection, cloning, sequencing, amplification, hybridisation, cDNA synthesis, studying nucleic acid structure and composition (e.g. the methylation pattern of DNA) etc. can be undertaken; the presence of large amounts of cellular or other contaminating material e.g. proteins or carbohydrates, in such complex mixtures often impedes many of the reactions and techniques used in molecular biology. In addition, DNA may contaminate RNA preparations and vice versa. Thus, methods for the isolation of nucleic acids from complex mixtures such as cells, tissues etc. are demanded, not only from the preparative point of view, but also in the many methods in use today which rely on the identification of DNA or RNA e.g. diagnosis of microbial infections, forensic science, tissue and blood typing, genotyping, detection of genetic variations etc. The purification of DNA or RNA from more enriched but still contaminated samples is also desirable, e.g. to purify synthetically prepared nucleic acid material, e.g. to purify PCR products from contaminating salts, excess primers and/or dNTPs.

Particularly in the fields of nucleic acid diagnostics, population studies and genotyping, it is important to obtain high quality and pure nucleic acid preparations to ensure that further amplification and/or detection steps are reliably and accurately carried out.

In RNA identifications it is important for a conclusive diagnosis to be certain that the detected sequence is derived from an RNA molecule and not from genomic DNA contamination in the sample. For this reason, methods for the separation of RNA from DNA are important. Also, for RNA isolation rapid methods are required since RNA molecules usually are very unstable and rapidly degraded by RNases present in cells and body fluids. The quality of the RNA is probably the most important factor in determining the quality of the final results in protocols utilising mRNA, especially for cDNA synthesis. It is important to avoid DNA contamination of RNA preparations for a number of reasons. Firstly, DNA increases viscosity making sample handling difficult leading to poor RNA yield and also RNA of poor quality with the likelihood of DNA contamination. Also, DNA contamination may trap RNase enzymes and make downstream applications such as RT-PCR worthless.

A range of methods are known for the isolation of nucleic acids, but generally speaking, these rely on a complex series of extraction and washing steps and are time consuming and labourious to perform. Moreover, the use of materials such as alcohols and other organic solvents, chaotropes and proteinases is often involved, which is disadvantageous since such materials tend to interfere with many enzymic reactions and other downstream processing applications.

Thus, classical methods for the isolation of nucleic acids from complex starting materials such as blood or blood products or tissues involves lysis of the biological material by a detergent or chaotrope, possibly in the presence of protein degrading enzymes, followed by several extractions with organic solvents e.g. phenol and/or chloroform, ethanol precipitation, centrifugations and dialysis of the nucleic acids. The purification of RNA from DNA may involve a selective precipitation with LiCl or a selective isolation with acidic guanidinium thiocyanate combined with phenol extractions and ethanol precipitation. Not only are such methods cumbersome and time consuming to perform, but the relatively large number of steps required increases the risk of degradation, sample loss or cross-contamination of samples where several samples are simultaneously processed. In the case of RNA isolation, the risk of DNA contamination is relatively high.

In purification of RNA, it is commonly desired to specifically isolate mRNA. Most mRNA purification strategies involve isolation of total RNA and fractionation of the isolated RNA. Preparation of high-quality mRNA is an important step in the analysis of gene structure and gene regulation.

Most eukaryotic mRNAs have a poly(A)tail, typically about 50 to 300 nucleotides long. Such mRNA is referred to as polyadenylated or poly(A)$^+$ mRNA. In separating this polyadenylated RNA from the non-adenylated RNA which accounts for 95% or more of a cell's total RNA, advantage is taken of this poly(A) tail and some type of affinity separation directed toward the poly(A) tail is performed. The conventional technology has involved purification of total RNA as a first step and selection of poly(A)$^+$ RNA by affinity chromatography using oligo(dT)-cellulose as the second step. This strategy, is rather time-consuming and labour-intensive. An alternative strategy for mRNA purification is to use oligo(dT) linked to solid supports such as microplates, latex, agarose or magnetic beads.

Over the past few years it has become increasingly popular to employ a magnetic bead assisted strategy for poly(A)$^+$ RNA selection since such beads have proven to be favourable in mRNA manipulations. In many approaches, the yield and the quality of the products depends on how rapidly the mRNA can be purified from nucleases and other contaminants. By using the magnetic bead separation technology, pure, intact poly(A)$^+$ RNA can be obtained rapidly either from total RNA preparations or more importantly, directly from crude lysates of solid tissues, cell or body fluids. The entire procedure can be carried out in a microfuge tube without phenol extractions or ethanol precipitations.

One approach common in RNA purification, which may be used in conjunction with the solid phase approach is to carry out the lysis of the biological material and the subsequent hybridisation to oligo dT in LiCl and LiDS/SDS buffers, thereby avoiding extra steps such as phenol extraction or proteinase-K digestion. The whole direct mRNA isolation takes approximately 15 minutes and since the mRNA is stable for more than 30 minutes in the lysis buffer, this ensures the high quality of the mRNA purified. However, a disadvantage of this method is that mRNA per weight unit of tissue is affected by the amount of tissue used and above a critical threshold of lysed cells, the yield of mRNA decreases.

Another common approach for direct mRNA purification is, as mentioned above, to use guanidinium isothiocyanate (GTC) and sarkosyl. A GTC-buffer system is preferred by most researchers due to the ability of this chaotropic salt to inhibit RNases. This may also be used in combination with the magnetic bead approach. However, the viscosity of cell lysates in 4M GTC is high and the beads are not effectively attracted by the magnet, resulting in an increased risk for DNA contamination, both for beads and other solid phases, and lower yields.

More recently, other methods have been proposed which rely upon the use of a solid phase. U.S. Pat. No. 5,234,809, for example, describes a method where nucleic acids are bound to a solid phase in the form of silica particles, in the presence of a chaotropic agent such as a guanidinium salt, and thereby separated from the remainder of the sample. WO 91/12079 describes a method whereby nucleic acid is trapped on the surface of a solid phase by precipitation. Generally speaking, alcohols and salts are used as precipitants.

U.S. Pat. Nos. 5,705,628 and 5,898,071 describe methods of isolating nucleic acid fragments using a combination of large molecular weight polyalkylene glycols (e.g. polyethylene glycols) at concentrations of from 7 to 13% with salt in the range of 0.5 to 5M to achieve binding to functional groups on a solid support which acts as a bioaffinity absorbent for DNA.

Although such methods generally speed up the nucleic acid separation process, there are disadvantages associated with the use of alcohols, chaotropes, salts, large molecular weight molecules and other similar agents.

Large molecular weight molecules increase the viscosity of the liquid which reduces the efficiency with which purification protocols can be conducted. In the case of separation of magnetic beads, such large molecules reduce the speed of isolation as the time of contact with the magnet to separate the beads has to be increased. Furthermore, the removal of supernatant in such systems is more difficult in the presence of the large molecular weight molecules.

Chaotropes need to be used at high molarity, resulting in viscous solutions which may be difficult to work with, especially in RNA work. Amplification procedures such as PCR, and other enzyme-based reactions, are very sensitive to the inhibitory or otherwise interfering effects of alcohols and other agents. Moreover, the drying of the nucleic acid pellet which is necessary following alcohol precipitation and the problems with dissolving nucleic acids, are also known to lead to artefacts in enzyme-based procedures such as PCR.

Since such procedures are now a mainstay of molecular biology, there is a need for improved methods of nucleic acid isolation, and particularly for methods which are quick and simple to perform, which enable good yields to be obtained without losses, and which avoid the use of solvents and chaotropic agents or alcohol precipitation or the use of high levels of salt and/or high molecular weight compounds with high viscosity. There is also a need for a method which allows for differentiation between RNA and DNA and permits a separate isolation of both types of nucleic acid from the same sample. The present invention seeks to provide such methods.

In particular, it has now been found that nucleic acid may be isolated from a sample in a form suitable for amplification or other downstream processes such as sequencing or other analyses after amplification, by a simple and easy to perform procedure which involves treating the sample with detergent (if required) and allowing the nucleic acid to bind to a solid support in the presence of high levels of a molecule consisting of from 2 to 70 ethylene oxide units (e.g. tetraethylene glycol), whereupon the nucleic acid may be readily separated from the sample, e.g. by removal of the support. The binding of the nucleic acid is independent of its sequence.

In one aspect, the present invention thus provides a method of isolating nucleic acid from a sample, said method comprising contacting said sample with a solid support in the presence of a molecule consisting of from 2 to 70 ethylene oxide units (preferably an oligoethylene glycol, especially preferably tetraethylene glycol (TETRA EG or TEG as referred to herein)), whereby soluble nucleic acid in said sample is bound to the surface of the support, and separating said support with bound nucleic acid from the sample.

Molecules for use in accordance with the invention are multimers consisting of from 2 to 70 ethylene oxide (ie —O—$CH_2$—$CH_2$) units, preferably in linear arrangement, i.e. with a molecular weight of from around 100 to 3100. Such molecules are referred to herein as ethylene glycol multimers and have the general formula H—(O—$CH_2$—$CH_2$)$_n$—OH, where n is the number of ethylene oxide units. Preferred molecules have from 2 to 60, 50, 40, 30 or 20 monomers. Compositions containing ethylene glycol multimers, particular in the case of the larger multimers, by their very nature are likely to comprise multimers of variable length. The size of the multimers referred to herein refers to the average number of monomers found in the multimers in a composition. One or more molecules having from 2 to 70 monomers may be used in a solution (i.e. a mix of multimers with one specified average length together with multimers with a second specified average length, may be used). Preferred molecules according to the invention are multimers with from 2 to 10 monomers, referred to herein as oligoethylene glycols. An oligoethylene glycol as referred to herein has 10 or fewer (i.e. 9, 8, 7, 6, 5, 4, 3 or 2) ethylene oxide units and a molecular weight of less than 460. Especially preferably said oligoethylene glycol has between 2 and 6 (or between 3 and 6) ethylene oxide units, e.g. tetraethylene glycol.

The ethylene glycol multimer is used at a final concentration of 10-90% in the final mix of the sample and solid support. The concentration as expressed for ethylene glycol multimers is w/v or v/v depending on whether these molecules are solid or liquid at room temperature. For oligoethylene glycols, for example, which are liquid at room temperature, the concentrations are expressed as v/v. Preferably a final concentration of greater than 15, 20 or 30%, e.g. 15-35, 20-40 or 30-75%, e.g. 45-60% is used. TEG as referred to herein has the formula $HOCH_2CH_2(OCH_2CH_2)_3OH$ and may be obtained from Sigma-Aldrich Co., Fluka#86660 or 86662, or Aldrich #11, 017-5.

TEG and other oligoethylene glycols used according to the invention may be generated by appropriate synthetic protocols. For example, di, tri and tetraethylene glycols and other oligoethylene glycols may be produced by hydration of ethylene oxide. Larger molecules may be generated by polymerization of ethylene glycol.

In a preferred aspect the binding reaction is preferably conducted in the presence of salt. Salt is preferably at levels less than 1M (at its final concentration), e.g. from 5, 10, 20 or 50 mM to less than 0.5, 0.4, 0.3, 0.2 or 0.1 M. This may vary depending on the particular salt/cation that is used. For example $Mg^{2+}$ may be used in the range 5-50 mM (final concentration, preferably around 15 mM) and $Na^+$ may be used in the range 0.5-1M (final concentration). Other ions that may be used include $Ba^{2+}$, $Ca^{2+}$, $K^+$ and $Li^+$, e.g. as chloride salts.

Optionally said sample may be contacted with a detergent before, simultaneously or after contact of said sample with the ethylene glycol multimer. Use of a detergent is particularly desirable when complex and/or impure samples are used as the starting material. Especially preferably the sample is contacted with the ethylene glycol multimer, but is not contacted with one or more of the following (or they are present at only low levels):

detergents;
chaotropes; and
alcohols, such as ethanol.

Especially preferably the ethylene glycol multimer is used alone for example in a simple buffer solution (optionally also containing salt as described above), e.g. at 15-35%. Detergents, chaotropes and/or alcohols may however be present in small or trace amounts. Where present, detergent is preferably present at a level as described hereinafter, e.g. 0.2 to 30% (w/v). However low levels, e.g. less than 1 or less than 0.5 or 0.2% detergent may be present.

Chaotropes are preferably entirely absent.

Alcohol levels are preferably less than 300 (v/v), e.g. less than 20, 10, 5, 3, 2 or 1% (final concentration once added to the sample and including any contribution made by liquid associated with the solid support once added). Where present, alcohol may be present at e.g. 1 to 30%, e.g. from 5 to 10 or 20%. Higher levels of alcohol lead to the capture of small oligonucleotides which is generally undesirable, particularly in methods of the invention in which the nucleic acid molecules are to be separated from contaminating oligonucleotides e.g. to allow the separation of amplified products from primers.

Thus the invention particularly provides methods which allow the separation of nucleic acid molecules of greater than 100 base pairs from oligonucleotides of shorter lengths, e.g. less than 30 nucleotides.

Especially preferably the present invention provides a method of isolating nucleic acid from a sample, said method comprising contacting said sample with a solid support in the presence of 15-35% of an ethylene glycol multimer (preferably an oligoethylene glycol, especially preferably tetraethylene glycol (TEG)), (and optionally a salt concentration of less than 1M, e.g. from 5 mM to 0.5M (preferably 5-30 mM)) and an alcohol concentration of less than 30% (preferably less than 10%), whereby soluble nucleic acid in said sample is bound to the surface of the support, and separating said support with bound nucleic acid from the sample.

Preferably said method additionally comprises elution of said nucleic acid material from the solid support and optionally the performance of further downstream processes such as sequencing on said eluted material.

The nucleic acid may be DNA, RNA or any naturally occurring or synthetic modification thereof (e.g. PNA), and combinations thereof. Preferably however the nucleic acid will be DNA, which may be genomic, or, cDNA, and single or double stranded or in any other form, e.g. linear or circular. Especially preferably said nucleic acid molecules are amplification products, e.g. of PCR. In a preferred aspect, non-genomic DNA fragments are isolated, e.g. having a size of from 10 base pairs to 250 kb, especially preferably molecules from 100 bp to 10 kb may be isolated.

Amplification procedures as referred to herein include any processes which increase the levels of the nucleic acid molecule or its complementary sequence by in vitro processes and include techniques such as LAR, 3SR and the Q-beta-replicase system. However, PCR and its various modifications e.g. the use of nested primers, will generally be the method of choice (see e.g. Abramson and Myers, 1993, Current Opinion in Biotechnology, 4: 41-47 for a review of nucleic acid amplification technologies).

Where the method of the invention is used to isolate DNA, it may conveniently be coupled with a further step to isolate RNA from the same sample. The use of the method in such two-step RNA separations will be described in more detail below.

The samples may be any material containing nucleic acid, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, urine, faeces, cerebrospinal fluid or any other body fluids, tissues, cell cultures, cell suspensions etc.

Preferably however, the sample is a relatively pure starting material such as an amplification product after performance of an amplification process, e.g. a PCR product, or a semi-pure preparation obtained by other nucleic acid recovery processes. The method may also be used to purify other non-genomic DNA such as plasmids, cosmids and other DNA fragments. These may conveniently be present after separation using techniques such as electrophoresis and the nucleic acid material isolated after such separation. Thus for example the sample is preferably substantially devoid of cellular components such as membranes and contains only genetic material (or copies thereof) derived from the cells from which the sample is generated. Especially preferably the sample is devoid of chromosomal DNA, proteins and membranes of the cells from which it was derived.

The nucleic acid-containing sample may, generally speaking, simply be contacted with the ethylene glycol multimer containing solution, and a solid phase which may be added to the sample prior to, simultaneously with, or subsequently to the ethylene glycol multimer. (Preferably the ratio of sample, e.g. PCR sample:ethylene glycol multimer containing solution is approximately 1:1.) If necessary, this may be preceded by one or more separate steps to disrupt structural components such as cell walls or to achieve lysis. Procedures for achieving this are well known in the art. Thus, for example, some cells e.g. blood cells, may be lysed by the additional use of detergent. Other cells, e.g. plant or fungal cells or solid animal tissues may also require more vigorous treatment such as, for example, grinding in liquid nitrogen, heating in the presence of detergent, alkaline lysis in the presence of detergent. For samples in the form of paraffin sections and such like, lysis (and melting of the paraffin) may be effected by heating, for example using a microwave oven (Banerjee, S. K. et al., 1995, Biotechniques 18: 769-773). Also, certain more compact tissues may require enzyme treatment, for example using proteinase K to obtain sufficient release of nucleic acid. The various components are mixed and simply allowed to stand for a suitable interval of time to allow the nucleic acid to bind to the support. Conveniently, if other agents such as enzymes e.g. proteinase K are being used, they may be included in with the ethylene glycol multimer or detergent, if the latter is used. The support is then removed from the solution by any convenient means, which will depend of course on the nature of the support, and includes all forms of withdrawing the support away from the sample supernatant, or vice versa, for example centrifugation, decanting, pipetting etc.

The conditions during this process are not critical, and it has been found convenient, for example, simply to mix the sample with the ethylene glycol multimer in the presence of a solid phase, and allow it to stand at room temperature, e.g. 15-25° C., e.g. around 20° C., for 30 seconds to 20 minutes, e.g. 2-10 minutes before separating. Longer incubation times may be used to maximize the yield of longer nucleic acid molecules. As mentioned above, the reaction time is not critical and as little as 5 minutes is often enough. However, if convenient, longer periods may be used, e.g. 0.5 to 3 hours, or even overnight. Mixing can be performed by any convenient means, including for example simple agitation by stirring or vortexing. Also, if desired, higher or lower temperatures may be used, but are not necessary.

Where used, the detergent may be any detergent, and a vast range are known and described in the literature. Thus, the detergent may be ionic, including anionic and cationic, non-ionic or zwitterionic. The term "ionic detergent" as used herein includes any detergent which is partly or wholly in ionic form when dissolved in water. Anionic detergents have been shown to work particularly well and are preferred. Suitable anionic detergents include for example sodium dodecyl sulphate (SDS) or other alkali metal alkylsulphate salts or similar detergents, sarkosyl, or combinations thereof.

Conveniently, the detergent may be used in a concentration of 0.2 to 30% (w/v), e.g. 0.5 to 30%, preferably 0.5 to 15%, more preferably 1 to 10$. For anionic detergents concentrations of 1.0 to 5% e.g. 0.5 to 5% have been shown to work well.

Conveniently the detergent may be incubated with the sample at room temperature or at higher temperatures e.g. 37° C., 50° C. or 65° C. to achieve lysis. Likewise, the time of incubation may be varied from a few minutes e.g. 5 or 10 minutes to hours, e.g. 20 to 40 minutes or 1 to 2 hours. For enzymatic lysis, e.g. using proteinase K etc, longer treatment times may be required, e.g. overnight.

The detergent may be supplied in simple aqueous solution, which may be alkaline or acidic, or more preferably in a buffer.

The ethylene glycol multimer and optionally also the detergent if present may be provided in any suitable buffer, including for example Tris, Bicine, Tricine, and phosphate buffers. Preferably, as mentioned above, a source of monovalent cations, e.g. a salt, may be included to enhance nucleic acid capture, although this may not always be necessary. Suitable salts include chloride salts, e.g. magnesium chloride, sodium chloride, lithium chloride etc. at concentrations of 0.1 to 1M, e.g. 250 to 500 mM. Lower concentrations, e.g. of less than 200 mM, e.g. from 5 to 50 mM salt may also be used. The above concentrations refer to the final concentration in the sample:bead:ethylene glycol multimer solution mix. As mentioned above, other components such as enzymes, may also be included.

Other optional components in the ethylene glycol multimer containing composition include chelating agents e.g. EDTA, EGTA and other polyamino carboxylic acids conveniently at concentrations of 1 to 50 mM etc., reducing agents such as dithiotreitol (DTT) or β-mercaptoethanol, at concentrations of for example 1 to 10 mM.

Preferred TEG compositions may for example comprise:
10 mM Tris-HCl pH 7.5
10 mM EDTA
40% TEG
or:
10 mM Tris-HCl pH 7.5
50% TEG
30 mM MgCl$_2$
or:
10 mM Tris-HCl pH 7.5
60% TEG
30 mM MgCl$_2$
2% SDS
or:
10 mM Tris-HCl pH 7.5
40% TEG
mM MgCl$_2$
20% EtOH These solutions are the stock solutions that are preferably used at a ratio of 1:1 with the sample and thus the relative amounts of each constituent in the final solution would be halved.

Without wishing to be bound by theory, it is believed that the ethylene glycol multimer (and the salt where present) destroys hydrogen bonds between water and the nucleic acid molecules allowing the latter to become associated with the solid support and form a less solvated structure. An ion bridge may then be formed by a cation between the charged solid support and the charged nucleic acid molecule.

The detergent, where present, functions in the method to lyse the nucleic acid containing material, e.g. the cells and nuclei to release the nucleic acid. The detergent is also believed to help to disrupt the binding of proteins, e.g. DNA-binding proteins, to the nucleic acid and to reduce the problem of contaminants in the sample sticking to the solid support if impure or highly complex samples are employed.

The solid support may be any of the well known supports or matrices which are currently widely used or proposed for immobilisation, separation etc. These may take the form of particles, sheets, gels, filters, membranes (e.g. nylon membranes), fibres, capillaries, needles or microtitre strips, tubes, plates or wells, etc, combs, pipette tips, micro arrays, chips, or indeed any solid surface material.

Conveniently the support may be made of glass, silica, latex, plastic or a polymeric material. Preferred are materials presenting a high surface area for binding of the nucleic acid. Such supports will generally have an irregular surface and may for example be porous or particulate, e.g. particles, fibres, webs, sinters or sieves. Particulate materials e.g. beads are generally preferred due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10 and more preferably not more than 6 μm. For example, beads with a diameter of 1 μm, 2.8 μm or 4.5 μm may be used.

Monodisperse particles, that is those which are substantially uniform in size (e.g. having a diameter standard deviation of less than 5%) have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dynal Biotech ASA (Oslo, Norway) as well as from Qiagen, Amersham Pharmacia Biotech, Serotec, Seradyne, Merck, Nippon Paint, Chemagen, Promega, Prolabo, Polysciences, Agowa and Bangs Laboratories.

However, to aid manipulation and separation, magnetic beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the nucleic acid binding step, and is a far less rigorous method than traditional techniques such as centrifugation which generate shear forces which may degrade nucleic acids.

Thus, using the method of the invention, the magnetic particles with nucleic acid attached may be removed onto a suitable surface by application of a magnetic field e.g. using a permanent magnet. It is usually sufficient to apply a magnet to the side of the vessel containing the sample mixture to aggregate the particles to the wall of the vessel and to pour away the remainder of the sample.

Especially preferred are superparamagnetic particles as magnetic aggregation and clumping of the particles during reaction can be avoided, thus ensuring uniform and nucleic acid extraction. Such particles are for example described by Sintef in EP-A-106873. The well-known magnetic particles sold by Dynal Biotech ASA (Oslo, Norway) as DYNA-BEADS®, are particularly suited to use in the present invention.

Solid supports which may be used include any solid support whose surface is relatively hydrophilic and is neutral or has a net negative charge at the pH at which the method is performed. Preferred pHs for performance of the method are from 4 to 9. Preferably such solid supports contain groups which can participate in complexation with the nucleic acid. Appropriate solid supports include those made of, or coated with, silica, polyurethane, epoxy groups and carbohydrates.

Depending on the choice of solid support, it may be used without the addition of functional groups or may be modified to provide such groups.

Functionalised coated particles for use in the present invention may be prepared by modification of the beads according to U.S. Pat. Nos. 4,336,173, 4,459,378 and 4,654,267. Thus, beads, or other supports, may be prepared having different types of functionalised surface. Especially preferably solid supports, such as magnetic beads, which are not hydrophilic and/or do not carry a suitable group to complex with the nucleic acid, may be modified to carry a free functional group to which the nucleic acid may bind. Such a functional group may be a hydroxyl group, epoxy group, carboxylic acid or sulphonic acid. Preferred beads include silica coated beads and beads with hydrophilic surfaces such as those carrying acrylates or epoxides.

It is also possible to use solid supports which have been modified to permit the selective capture of desired cells, viruses etc. containing the nucleic acid, when the starting material is a relatively impure preparation. Thus for example, supports carrying antibodies, or other binding proteins, specific for a desired cell type may be used. This may introduce a degree of selectivity to the isolation of the nucleic acid, since only nucleic acid from a desired target source within a complex mixture may be separated. Thus for example, such a support may be used to separate and remove the desired cell type etc. from the sample, following which, detergent is added to achieve lysis and release of the nucleic acid and the ethylene glycol multimer is added to achieve binding to the support.

The preparation of such selective cell capture matrices is well known in the art and described in the literature.

Thus, in a preferred aspect the invention provides a method of isolating nucleic acid from a sample as described hereinbefore, wherein said sample contains cells (containing the nucleic acid of interest) and said cells are obtained by immunomagnetic separation, e.g. using a solid support (e.g. beads) carrying antibodies to antigens specific to a target cell. The solid support to which the cells bind may be the same or different to the solid support to which nucleic acid binds in accordance with the invention. Preferably the solid supports used for separating the cells are beads and thus after immunomagnetic separation the cells are present in a cell:bead complex, prior to nucleic acid isolation. In this method, as in other methods of the invention, the method may further comprise the additional step of isolating RNA from said sample.

Likewise, the support may be provided with binding partners to assist in the selective capture of nucleic acids. For example, complementary DNA or RNA sequences, or DNA binding proteins may be used, or viral proteins binding to viral nucleic acid. The attachment of such proteins to the solid support may be achieved using techniques well known in the art.

Although not necessary, it may be convenient to introduce one or more washing steps to the isolation method of the invention, for example following separation of the support from the sample. Preferably the method as described herein includes at least one washing step as described hereinafter. In the case of magnetic beads, this may conveniently be performed before releasing the DNA from the beads. Especially preferably, the first (and optionally subsequent) washing step (s) after binding of the nucleic acid material are performed using solutions with less than 1M salt, preferably less 500 mM, e.g. less than 250, 100 or 50 mM salt. In one embodiment, the washing buffer may be the same as the buffer containing the ethylene glycol multimer, e.g. a TEG/salt mix. Especially preferably alcohol solutions of between 50 and 90% are used for washing, e.g. 70% ethanol, without any salt.

Following the separation step, and any optional washing steps which may be desired, the support carrying the nucleic acid may be transferred e.g. resuspended or immersed into any suitable medium e.g. water or low ionic strength buffer. Conveniently, elution efficiency may be enhanced by the addition of chelating agents, e.g. EDTA to remove excess cations, e.g. $Mg^{2+}$. Depending on the support and the nature of any subsequent processing desired, it may or may not be desirable to release the nucleic acid from the support.

In the case of a particulate solid support such as magnetic or non-magnetic beads, this may in many cases be used directly, for example in PCR or other amplifications, or for sequencing without eluting the nucleic acid from the support. Also, for many DNA detection or identification methods elution is not necessary since a large majority of the bound molecules' length will be available for hybridisation to oligonucleotides and for amplification.

However, if desired, elution of the nucleic acid may readily be achieved using known means, for example by heating, e.g. to 65° C. for 5 to 10 minutes, or simply room temperature, e.g. for 1 to 10 minutes, e.g. 2 to 4 minutes, in water or a low ionic strength medium (which does not contain an ethylene glycol multimer), e.g. 10-30 mM tris-HCl, pH 7.5 buffer. Conveniently elution may be performed in a small volume to concentrate the isolated nucleic acid.

Following elution the support may be removed from the medium leaving the nucleic acid in solution.

As mentioned previously, the method is conveniently used for the isolation of amplification products. The method of the invention effectively remove primers from the desired amplification products such that their level of contamination is less than 10%, e.g. less than 5 or 1%. Yields of more than 85% for fragments over 1 kp and more than 40%, e.g. more than 60% for fragments of 100 bp are preferably achieved. If it is desired to remove RNA from DNA, this may be achieved by destroying the RNA before the DNA separation step, for example by addition of an RNAase or an alkali such as NaOH.

Alternatively, as mentioned above, the method of the invention may be used to separate sequentially DNA and RNA from the sample. It may also be used to remove DNA from a sample in an RNA purification procedure.

Conveniently, the sequential separation may take place using two different solid phases, for example solid supports which can differentiate between DNA and RNA. Thus, such a method may comprise carrying out a first step separation to isolate DNA as described above. A further solid support can then be added to the sample to capture the RNA remaining in the sample, either by using a solid support that can bind the RNA or any remaining nucleic acid, or a solid support that can capture specific RNA molecules (e.g. by carrying a complementary nucleic acid probe), or a subset of RNA molecules e.g. polyadenylated RNA. In this way it is possible to rapidly isolate and separate DNA and RNA or subsets of both from the same sample. This may be useful, for example by measuring the isolated DNA to estimate the amount of cells used for RNA extraction, which will give a reference between different samples.

However, the DNA isolation procedure of the invention may also readily be combined, as a preliminary step, with other conventional RNA purification procedures, for example DNA isolation with the ethylene glycol multimer according to invention may be carried out before a selective RNA precipitation step, for example using LiCl or before RNA separation using GTC and sarkosyl.

In a representative procedure, the sample is optionally lysed in the presence of detergent and the DNA is allowed to bind to a solid support in the presence of the ethylene glycol multimer, whereupon the DNA may readily be separated from the sample by removal of the support. If desired, the DNA can rapidly and easily be further handled for amplification or other downstream processes, such as sequencing. The RNA may then be isolated. This can be by a solid phase based system as described above, including a repetition of the method of the invention, or by conventional techniques such as extractions, precipitations or affinity chromatography.

A particularly advantageous embodiment of the invention is to use the isolation method of the invention to remove DNA from a sample prior to isolation of RNA, such that the viscosity of the lysed sample is reduced and a specific isolation of RNA molecules is favoured which again reduces or avoids the possibility of DNA contamination of the RNA. Such a method also has the advantage of being quick to perform.

The invention is advantageously amenable to automation, particularly if particles, and especially, magnetic particles are used as the support. Automated Liquid Handling Workstations such as Beckman Coulter Biomek®FX or Tecan Freedom EVO™ may be used for this purpose.

The various reactants and components required to perform the method of the invention may conveniently be supplied in kit form. Such kits represent a further aspect of the invention. At its simplest, this aspect of the invention provides a kit for isolating nucleic acid from a sample comprising a solid support and an ethylene glycol multimer. Preferably said solid support is a magnetic bead carrying carboxylic acid groups as free functional groups on said support.

Optionally included in such a kit may be buffers, detergents, alcohols, salts, lysis agents e.g. proteinases, chelating agents and reducing agents. The kit may be provided with instructions for use of the kit in accordance with the invention, e.g. included in a leaflet.

For isolation of RNA, the kits may further comprise means for isolating RNA e.g. a second solid support for isolating RNA, for example a support provided with probes for capture of RNA e.g. oligo dT or probes of complementary sequence to the desired target, or a chaotrope or selective precipitating agent.

BRIEF DESCRIPTION OF THE DRAWINGS

The invention will now be described in more detail in the following non-limiting Examples with reference to the drawings in which.

EXAMPLE 1

Effect of $MqCl_2$ in the DNA Isolation Protocol

Figure 1:
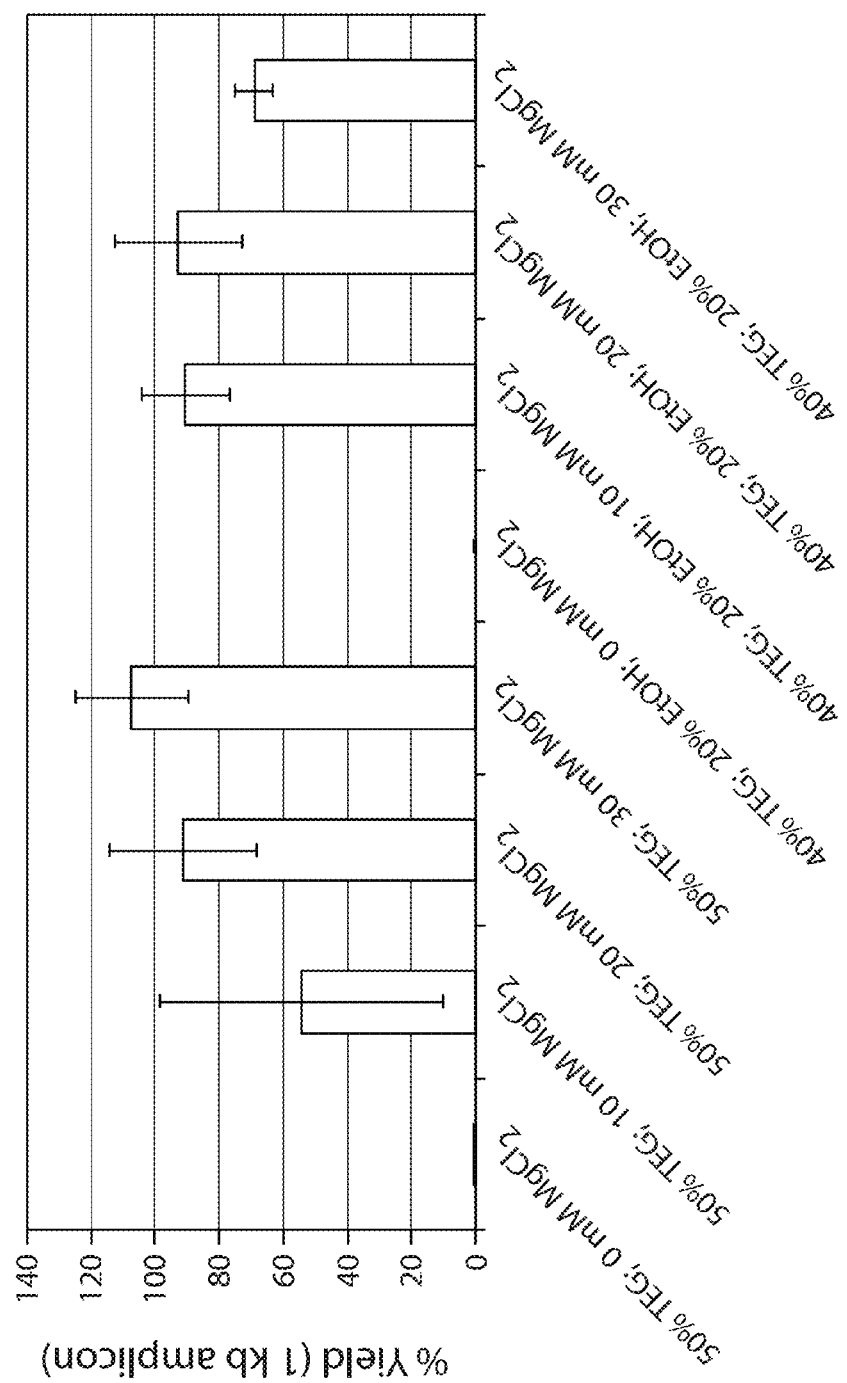
FIG. 1 shows the yield of PCR products when using various concentrations of TEG and $MgCl_2$ (wherein the values indicated refer to stock solutions and should be halved to derive the final concentration)

PCR Clean-Up reagent containing MyOne-COOH beads (2 mg/ml) and the reagents shown in FIG. 1 (20 µl) were added to non-purified PCR (20 µl). The mixture was incubated for 10 minutes, the supernatant removed and the beads washed in 70% Ethanol (50 µl). Water (20 µl) was added, the sample mixed and incubated for 2 minutes. The beads were separated by magnetic attraction and the supernatant transferred to a new tube.

The amount of amplicon in the supernatant was measured using the PicoGreen dsDNA detection Assay (Molecular Probes, Inc.). Yield of PCR product is stated as the percent of DNA detected in the non-purified starting material. (It has been shown that primers do not interfere with the PicoGreen detection reagent.)

It will be seen from FIG. 1 that $MgCl_2$ at a concentration of 10-30 mM (which equates to 5-15 mM final concentration) produces a good yield of the PCR products.

EXAMPLE 2

Efficiency of Primer Removal in the DNA Isolation Protocol

PCR Clean-Up reagent containing MyOne-COOH beads (2 mg/ml), 50% TEG and 30 mM $MgCl_2$ in 10 mM Tris pH 7.5 (20 µl) was added to non-purified PCR spiked with 10 pmol of a fluorescein labelled 20-mer oligonucleotide (20 µl). The mixture was incubated for 10 minutes, the supernatant removed and the beads washed in 70% Ethanol (50 µl). Water (20 µl) was added, the sample mixed and incubated for 2 minutes. The beads were separated by magnetic attraction and the supernatant transferred to a new tube.

The amount of fluorescent primer transferred in the supernatant was measured using VictorII (Perkin Elmer) plate reader at 485/515 nm.

Figure 2:
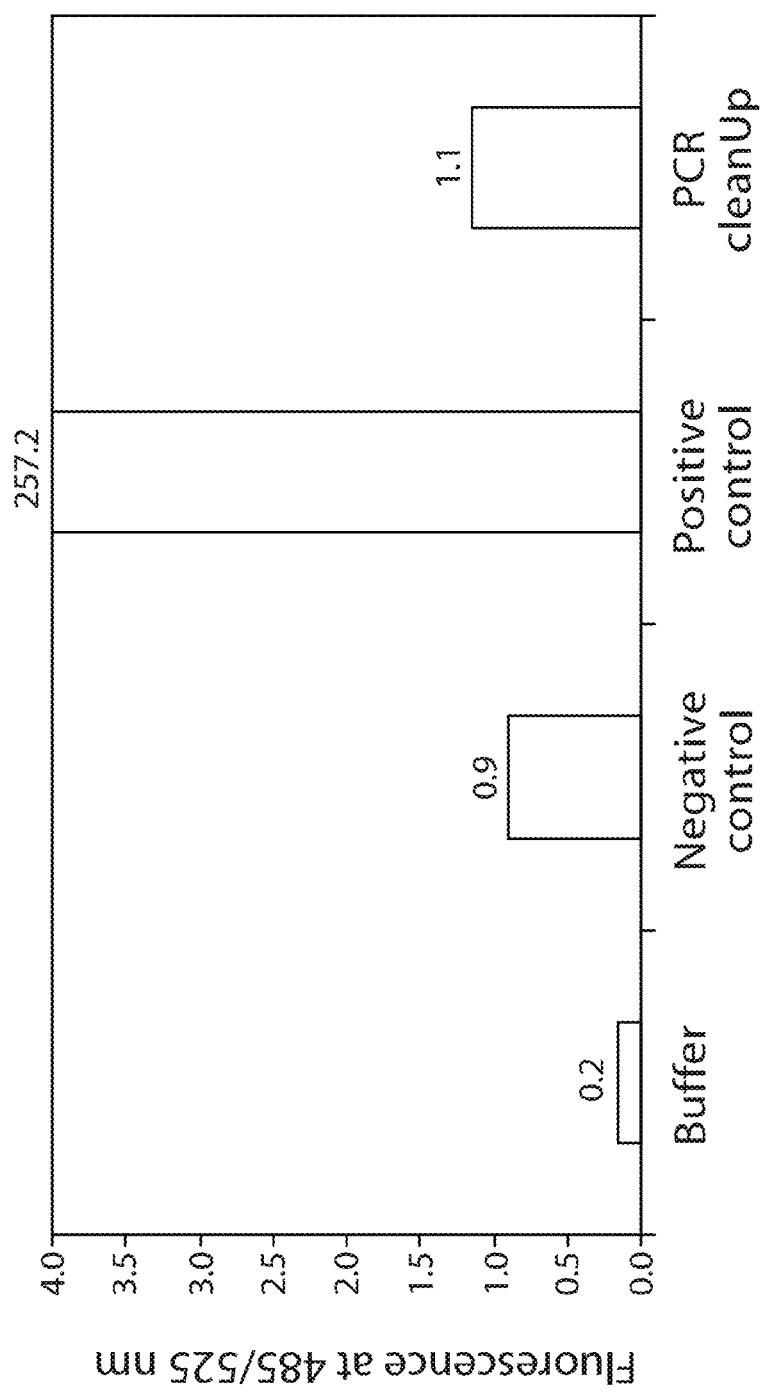
FIG. 2 shows the efficiency of primer removal using TEG for DNA isolation.

It will be seen from FIG. 2 that the isolation method was effective at removing contaminating primers.

EXAMPLE 3

Effect of TEG Concentration in the DNA Isolation Protocol

PCR Clean-Up reagent containing MyOne-COOH beads (2 mg/ml), 40-60 TEG and 30 mM $MgCl_2$ in 10 mM Tris pH 7.5 (20 μl) was added to a solution of a 100 bp ladder (20 μl) or non-purified PCR (20 μl). The mixture was incubated for 10 minutes, the supernatant removed and the beads washed in 70% Ethanol (50 μl). Water (20 μl) was added, the sample mixed and incubated for 2 minutes. The beads were separated by magnetic attraction and the supernatant transferred to a new tube.

PCR CleanUp using MyOne-COOH beads (2 mg/ml), 25% PEG-8000 and 30 mM MgCl$_2$ in 10 mM Tris pH 7.5 was used as a reference.

10 μl of the eluate was analysed by gel electrophoresis using 1.5 NuSieve agarose and ethidium bromide staining.

Figure 3:
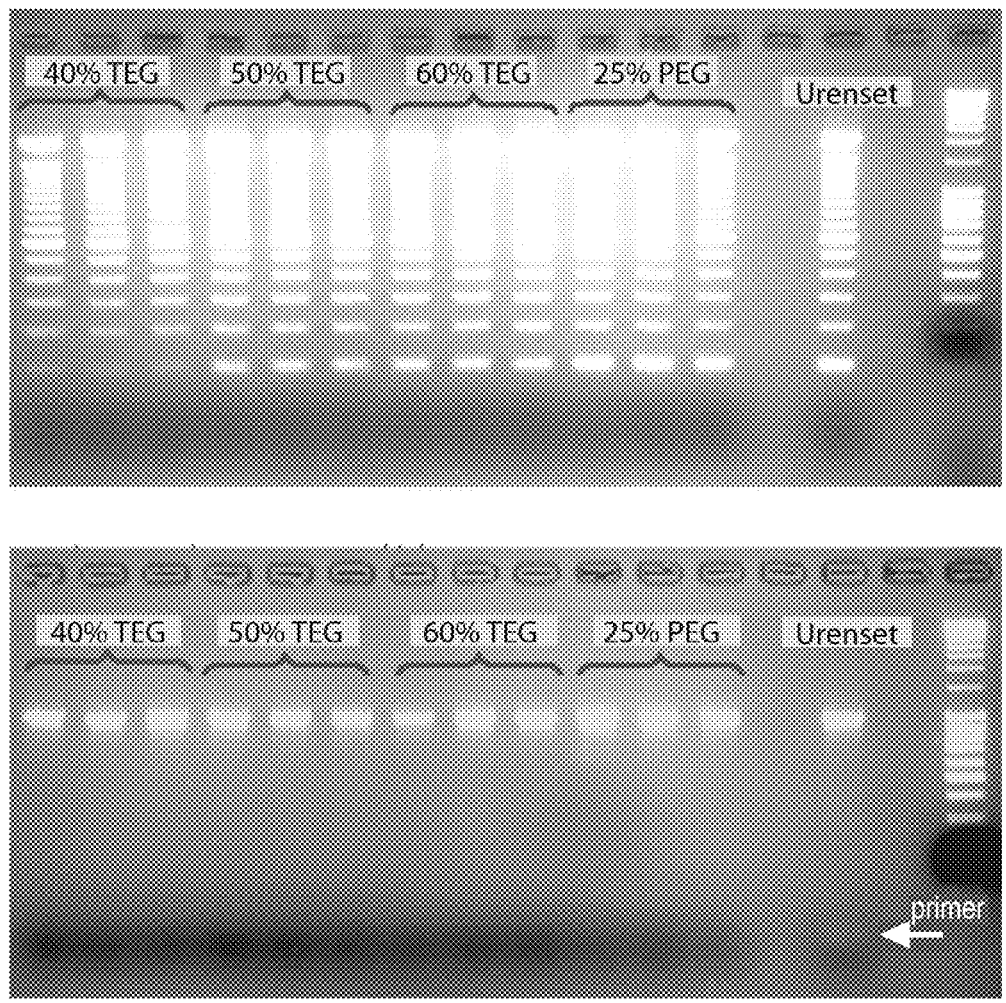
FIG. 3 shows the effect of TEG concentration in the DNA isolation protocol, wherein the values indicated refer to concentrations in stock solutions, and the top panel concerns a 100 bp ladder and the bottom panel concerns non-purified PCR products.

It will be seen from FIG. 3 that TEG at a final concentration of 20-30% was effective in PCR product isolation.

EXAMPLE 4

Effect of TEG and Ethanol Concentration in the DNA Isolation Protocol

PCR Clean-Up reagent containing MyOne-COOH beads (2 mg/ml), 40-50% TEG, 0-20% ethanol and 30 mM MgCl$_2$ in 10 mM Tris pH 7.5 (20 μl) was added to a solution of a 100 bp ladder (20 μl). The mixture was incubated for 10 minutes, the supernatant removed and the beads washed in 70% Ethanol (50 μl). Water (20 μl) was added, the sample mixed and incubated for 2 minutes. The beads were separated by magnetic attraction and the supernatant transferred to a new tube.

PCR CleanUp using MyOne-COOH beads (2 mg/ml), 25% PEG-8000 and 30 mM MgCl$_2$ in 10 mM Tris pH 7.5 was used as a reference.

10 μl of the eluate was analysed by gel electrophoresis using 1.5 NuSieve agarose and ethidium bromide staining.

Figure 4:
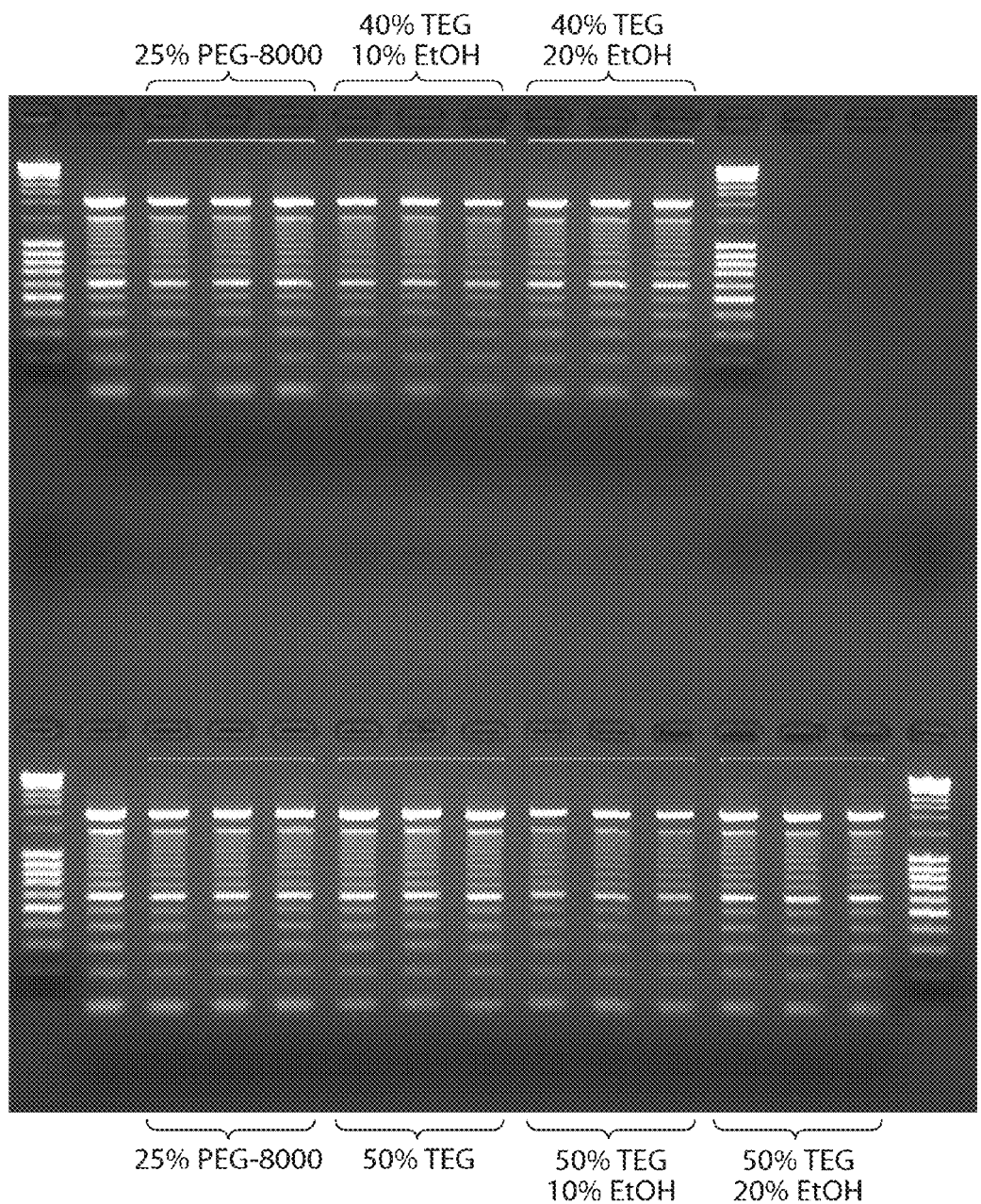
FIGS. 4 and 5 show the effect of TEG and ethanol concentration in the DNA isolation procedure, wherein the values indicated refer to concentrations in stock solutions.

It is apparent from FIG. 4 that the protocol is effective at TEG concentrations of 20 or 25% (final concentration) and ethanol concentrations of 0, 5 or 10% (final concentration).

EXAMPLE 5

Effect of TEG and Ethanol Concentration in the DNA Isolation Protocol

PCR Clean-Up reagent containing MyOne-COOH beads (2 mg/ml), 10-50% TEG, 0-40% ethanol and 30 mM MgCl$_2$ in 10 mM Tris pH 7.5 (50 μl) was added to a solution of a 100 bp ladder (50 μl). The mixture was incubated for 10 minutes, the supernatant removed and the beads washed in 70% Ethanol (1000 μl). Water (40 μl) was added, the sample mixed and incubated for 2 minutes. The beads were separated by magnetic attraction and the supernatant transferred to a new tube.

PCR CleanUp using MyOne-COOH beads (2 mg/ml), 25% PEG-8000 and 30 mM MgCl$_2$ in 10 mM Tris pH 7.5 was used as a reference.

10 μl of the eluate was analysed by gel electrophoresis using 1.5 NuSieve agarose and ethidium bromide staining.

Figure 5:
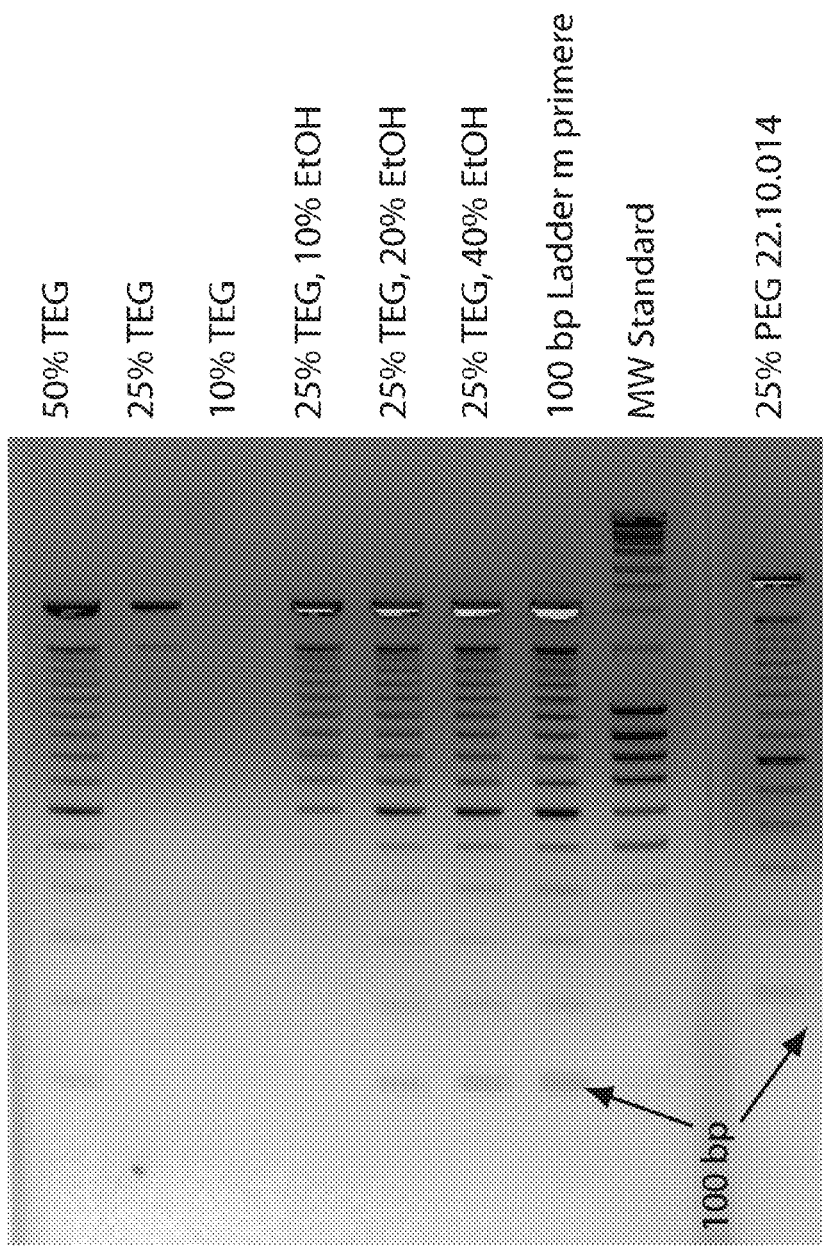

FIG. 5 shows that effective isolation is achieved using 25% TEG (final concentration) and that the isolation is effective without ethanol.

EXAMPLE 6

Effect of High Ethanol Concentrations and TEG in the DNA Isolation Protocol

Figure 6:
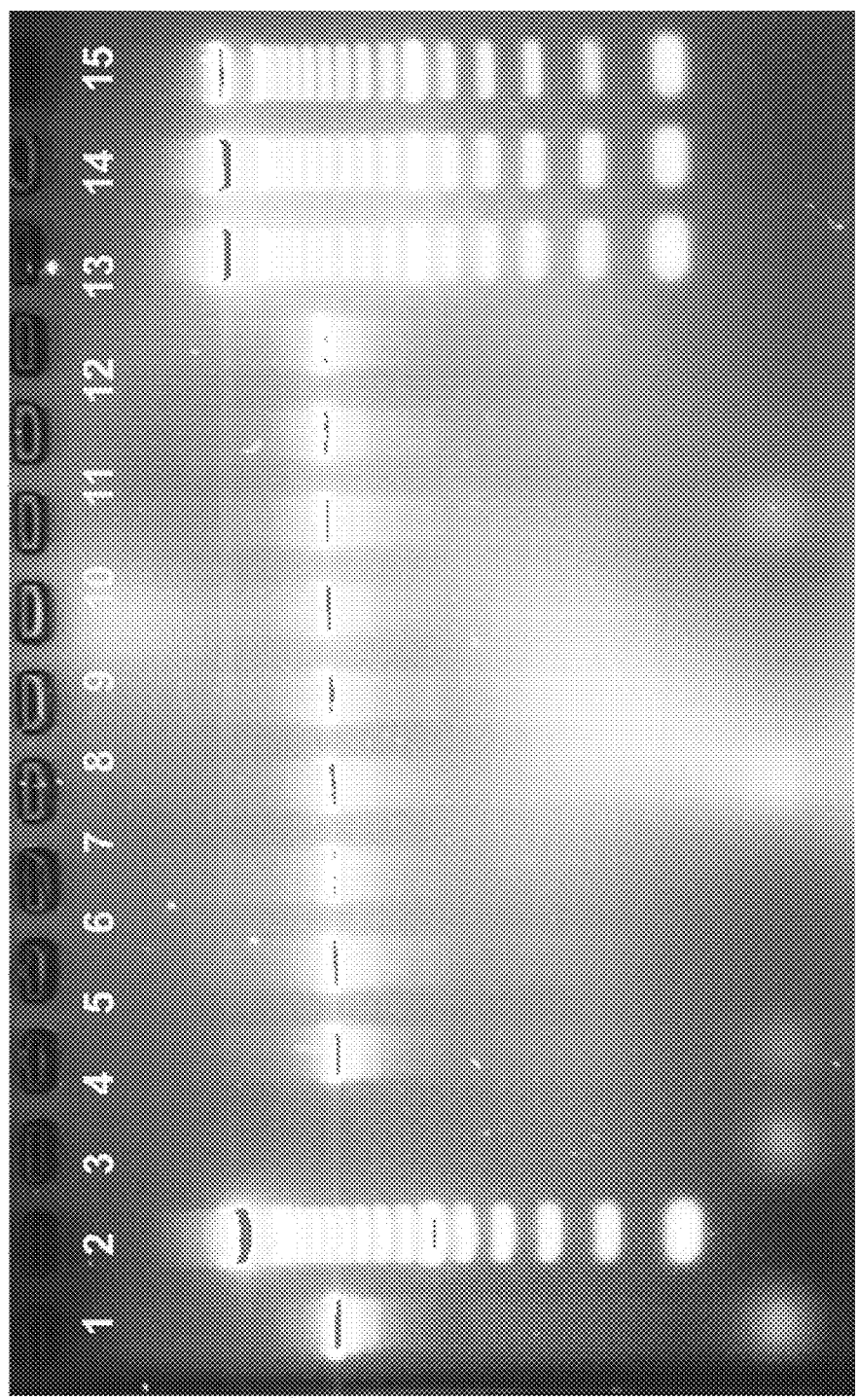
FIG. 6 shows the effect of TEG, PEG and high ethanol concentrations on the DNA isolation procedure, wherein the values indicated refer to concentrations in stock solutions. The lanes are as described in Example 6.

The methods were performed as described in previous examples. The lanes shown in FIG. 6 are as follows:
1. Crude PCR spiked with 20 pmol primer.
2. "Crude" 100 bp ladder.
3. "Crude" primer.
4, 7, 10. Purified PCR spiked with 20 pmol primer using MyOne-COOH beads (2 mg/ml), 25% TEG, 67% ethanol and 30 mM MgCl$_2$ in 10 mM Tris pH 7.5.
5, 8, 11. Purified PCR spiked with 20 pmol primer using MyOne-COOH beads (2 mg/ml), 50% TEG and 30 mM MgCl$_2$ in 10 mM Tris pH 7.5.
6, 9, 12. Purified PCR spiked with 20 pmol primer using MyOne-COOH beads (2 mg/ml), 25% PEG-8000 and 30 mM MgCl$_2$ in 10 mM Tris pH 7.5.
13. Purified 100 bp ladder using MyOne-COOH beads (2 mg/ml), 25% TEG, 67% ethanol and 30 mM MgCl$_2$ in 10 mM Tris pH 7.5.
14. Purified 100 bp ladder using MyOne-COOH beads (2 mg/ml), 50% TEG and 30 mM MgCl$_2$ in 10 mM Tris pH 7.5.
15. Purified 100 bp ladder using MyOne-COOH beads (2 mg/ml), 25% PEG-8000 and 30 mM MgCl$_2$ in 10 mM Tris pH 7.5.

The results are shown in FIG. 6 and show that the use of high levels of ethanol results in carry-over/co-purification of the primer (see lanes 4, 7 and 10) and is therefore undesirable.

The invention claimed is:

1. A method of isolating DNA from a sample comprising:
providing i) a sample that comprises nucleic acids, ii) an ethylene glycol multimer consisting of 2 to 10 ethylene oxide monomers, iii) a salt comprising a monovalent or a divalent metal ion, and iv) a solid support having a hydrophilic surface;
contacting the sample with the solid support in the presence of the ethylene glycol multimer and the salt under conditions to allow binding of DNA in the sample to the surface of the solid support to form a solid support with bound DNA; and
separating the solid support with bound DNA from the sample, thereby isolating DNA from the sample.

2. The method of claim 1, wherein the multimer consists of 3 to 6 ethylene oxide monomers.

3. The method of claim 1, wherein the multimer is an oligoethylene glycol with 10 or fewer ethylene oxide units.

4. The method of claim 1, wherein the multimer is an oligoethylene glycol with between 2 and 6 ethylene oxide units.

5. The method of claim 1, wherein the multimer is tetraethylene glycol.

6. The method of claim 1, wherein the method is performed in the presence of the ethylene glycol multimer at a final concentration of greater than 15%.

7. The method of claim 1, wherein the method is performed in the presence of the ethylene glycol multimer at a final concentration of 15-35%.

8. The method of claim 1, wherein binding the DNA to the solid support is in the presence of the salt at a final concentration of less than 1M.

9. The method of claim 1, wherein binding the DNA to the solid support is in the presence of the salt at a final concentration of 5 mM to 0.5M.

10. The method of claim 1, further comprising binding the DNA to the solid support in the presence of alcohol at a final concentration of less than 30% (v/v).

11. The method of claim 1, further comprising contacting the sample with a detergent, wherein the detergent is present at a final concentration of 0.2 to 30% (w/v).

12. The method of claim 11, wherein the detergent is an anionic detergent.

13. The method of claim 11, wherein the detergent is an alkali metal alkylsulfate salt.

14. The method of claim 1, further comprising binding the DNA to the solid support in the presence of less than 1% (w/v) detergent and less than 30% (v/v) ethanol.

15. The method of claim 1, wherein the contacting comprises contacting the sample and the solid support with a buffer solution, wherein the buffer solution consists essentially of a buffer and the ethylene glycol multimer.

16. The method of claim 1, further comprising separating DNA molecules of greater than 100 base pairs from oligonucleotides of less than 30 nucleotides comprising contacting the sample with final concentration of less than 30% (v/v) ethanol.

17. The method of claim 1, further comprising the step of eluting the DNA from the solid support with water or a low ionic strength medium.

18. The method of claim 17, wherein the DNA is non-genomic DNA fragments of from 10 base pairs to 250 kb.

19. The method of claim 1, wherein the sample is whole blood or a blood-derived product.

20. The method of claim 1, wherein the sample is a sample produced by an amplification process.

21. The method of claim 1, wherein the solid support is particulate.

22. The method of claim 1, wherein the solid support comprises magnetic beads.

23. The method of claim 1, wherein the solid support contains hydroxyl, epoxy, carboxylic acid, or sulfonic acid groups.

24. The method of claim 1, further comprising washing the solid support after binding of the DNA to the solid support with a buffer solution or an ethanol solution.

25. The method of claim 24, wherein washing the solid support after binding of the DNA comprises washing with a solution containing less than 250 mM salt and 50-90% ethanol, wherein the salt is selected from the group consisting of $Mg^{2+}$, $Ba^{2+}$, $Ca^{2+}$, $Na^+$, $K^+$, and $Li^+$ salts.

26. The method of claim 1, wherein the sample comprises cells, wherein the cells comprise DNA, and wherein the method further comprises lysing the cells to release DNA into the sample.

27. The method of claim 1, wherein the method is performed at a pH of from about 4 to 9 and the solid support has a neutral or a negative charge at that pH range.

28. The method of claim 1, wherein the salt is selected from the group consisting of $Mg^{2+}$, $Ba^{2+}$, $Ca^{2+}$, $Na^+$, $K^+$, and $Li^+$ salts.

29. A method for isolating nucleic acids from a sample comprising:
    providing i) a sample that comprises DNA, ii) an oligoethylene glycol multimer comprising 2 to 6 ethylene oxide units, iii) a salt comprising a monovalent or a divalent metal ion at a concentration of less than 1M, and iv) a solid support having a hydrophilic surface;
    contacting the sample with the solid support in the presence of the oligoethylene glycol multimer and the salt under conditions to allow binding of DNA in the sample to the surface of the solid support to form a solid support with bound DNA; and
    separating the solid support with bound DNA from the sample comprising
    removing the solid support with bound DNA from the sample, thereby isolating DNA from the sample.

30. The method of claim 29 wherein the oligoethylene glycol multimer is tetraethylene glycol.

31. A kit for isolating nucleic acids from a sample, the kit comprising:
    i) a solid support having a hydrophilic surface;
    ii) a salt comprising a monovalent or divalent metal ion; and
    iii) an ethylene glycol multimer consisting of 2 to 10 ethylene oxide monomers,
    wherein the nucleic acids comprise DNA.

32. The kit of claim 31, wherein the solid support is particulate.

33. The kit of claim 31, wherein the solid support comprises magnetic beads.

34. The kit of claim 31, wherein the solid support contains hydroxyl, epoxy, carboxylic acid, or sulfonic acid groups.

35. The kit of claim 31, wherein the ethylene glycol multimer is tetraethylene glycol.

36. The kit of claim 31, wherein the salt is selected from the group consisting of $Mg^{2+}$, $Ba^{2+}$, $Ca^{2+}$, $Na^+$, $K^+$, and $Li^+$ salts.

* * * * *

UNITED STATES PATENT AND TRADEMARK OFFICE
CERTIFICATE OF CORRECTION

PATENT NO. : 8,569,477 B2 Page 1 of 1
APPLICATION NO. : 11/815967
DATED : October 29, 2013
INVENTOR(S) : Erling Sigurd Finne It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this
Twenty-second Day of September, 2015

Michelle K. Lee
*Director of the United States Patent and Trademark Office*